(12) United States Patent
Anis et al.

(10) Patent No.: US 6,203,518 B1
(45) Date of Patent: Mar. 20, 2001

(54) REMOVAL OF TISSUE

(75) Inventors: Aziz Y. Anis, Lincoln, NE (US); Mark E. Steen, Chino Hills, CA (US)

(73) Assignee: Aziz Yehia Anis, Lincoln, NE (US)

(*) Notice: Subject to any disclaimer, the term of this patent is extended or adjusted under 35 U.S.C. 154(b) by 0 days.

(21) Appl. No.: 09/332,709

(22) Filed: Jun. 14, 1999

Related U.S. Application Data

(60) Division of application No. 08/828,928, filed on Mar. 28, 1997, now Pat. No. 5,911,699, which is a continuation-in-part of application No. 08/625,909, filed on Apr. 1, 1996, now Pat. No. 5,722,945, which is a continuation-in-part of application No. 08/372,866, filed on Jan. 13, 1995, now abandoned, which is a continuation of application No. 08/035,985, filed on Mar. 22, 1993, now abandoned, which is a continuation-in-part of application No. 07/759,937, filed on Sep. 16, 1991, now abandoned, which is a continuation of application No. 07/680,292, filed on Apr. 4, 1991, now abandoned, which is a continuation-in-part of application No. 07/553,975, filed on Jul. 17, 1990, now Pat. No. 5,222,959.

(51) Int. Cl.⁷ ..................................................... A61B 17/20

(52) U.S. Cl. ............................................. 604/22; 606/107

(58) Field of Search .................................... 606/107, 108, 606/180, 159, 170, 167; 604/22, 19

(56) References Cited

U.S. PATENT DOCUMENTS

| | | |
|---|---|---|
| 2,742,076 | 4/1956 | Klein . |
| 3,401,446 | 9/1968 | Obeda et al. . |
| 3,614,484 | 10/1971 | Shoh . |
| 3,683,736 | 8/1972 | Loose . |
| 3,809,977 | 5/1974 | Balamuth et al. . |
| 3,906,954 | 9/1975 | Baehr et al. . |
| 3,937,222 | 2/1976 | Banko . |
| 3,976,077 | 8/1976 | Kerfoot, Jr. . |
| 4,061,146 | 12/1977 | Baehr et al. . |
| 4,203,444 | 5/1980 | Bonnell et al. . |
| 4,273,128 | 6/1981 | Lary . |
| 4,316,465 | 2/1982 | Dotson, Jr. . |
| 4,320,761 | 3/1982 | Haddad . |
| 4,428,748 | 1/1984 | Peyman et al. . |
| 4,609,368 | 9/1986 | Dotson, Jr. . |
| 4,634,420 | 1/1987 | Spinose et al. . |
| 4,643,717 | 2/1987 | Cook et al. . |
| 4,732,156 | 3/1988 | Nakamura . |
| 4,747,820 | 5/1988 | Hornlein et al. . |
| 4,748,985 | 6/1988 | Nagasaki . |
| 4,749,376 | 6/1988 | Kensey et al. . |

(List continued on next page.)

FOREIGN PATENT DOCUMENTS

| 2 111 390 | 7/1983 | (GB) . |
|---|---|---|
| WO92/01423 | 6/1992 | (WO) . |

OTHER PUBLICATIONS

*Role of Atherectomy Catheters In Arterial Reconstruction*, Anthony D. Whittemore, MD, FACS, InterVentional Technologies, Inc.

*United States Defensive Publication*, Elmer J. Ballintine T102,001, Jul. 6, 1982.

*Primary Examiner*—Michael Buiz
*Assistant Examiner*—Kevin Truong
(74) *Attorney, Agent, or Firm*—Vincent L. Carney

(57) ABSTRACT

To reduce damage to surrounding tissue while fragmenting some tissue such as for example not damaging the capsular wall while removing the lens during cataract removal surgery or not damaging artery or vein walls during bypass surgery while freeing the artery or vein to be transplanted, an incision is made for the insertion of surface—a handpiece tip. The tip is rotated and reciprocated ultrasonically at the same time so that tissue is fragmented by the combined motion of a fragmenting surface perpendicular to the surface and at an angle to the surface many times during a single revolution or part of a revolution.

6 Claims, 9 Drawing Sheets

U.S. PATENT DOCUMENTS

| | | |
|---|---|---|
| 4,750,488 | 6/1988 | Wuchinich et al. . |
| 4,750,902 | 6/1988 | Wuchinich et al. . |
| 4,756,304 | 7/1988 | Watanabe . |
| 4,808,153 | 2/1989 | Parisi . |
| 4,820,156 | 4/1989 | Ross . |
| 4,828,052 | 5/1989 | Duran et al. . |
| 4,834,102 | 5/1989 | Schwarzchild et al. . |
| 4,838,853 | 6/1989 | Parisi . |
| 4,846,790 | 7/1989 | Hornlein et al. . |
| 4,880,011 | 11/1989 | Imade et al. . |
| 4,881,761 | 11/1989 | Hornlein et al. . |
| 4,885,004 | 12/1989 | Pao . |
| 4,898,575 | 2/1990 | Fishell et al. . |
| 4,917,085 | 4/1990 | Smith . |
| 4,936,281 | 6/1990 | Stasz . |
| 4,957,482 | 9/1990 | Shiber . |
| 4,979,952 | 12/1990 | Kubota et al. . |
| 4,986,827 * | 1/1991 | Akkas et al. .......................... 606/107 |
| 5,019,036 | 5/1991 | Stahl . |
| 5,042,461 | 8/1991 | Inoue et al. . |
| 5,112,299 | 5/1992 | Pascaloff . |
| 5,112,300 | 5/1992 | Ureche . |
| 5,114,399 | 5/1992 | Kovalcheek . |
| 5,158,564 | 10/1992 | Schnepp-Pesch et al. . |
| 5,935,096 * | 8/1999 | Barrett ................................ 606/107 |

* cited by examiner

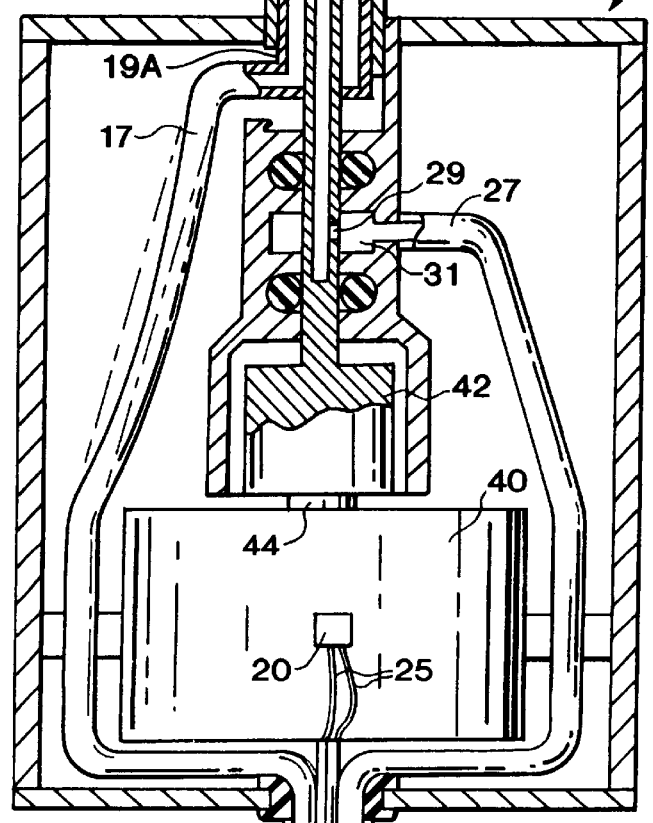
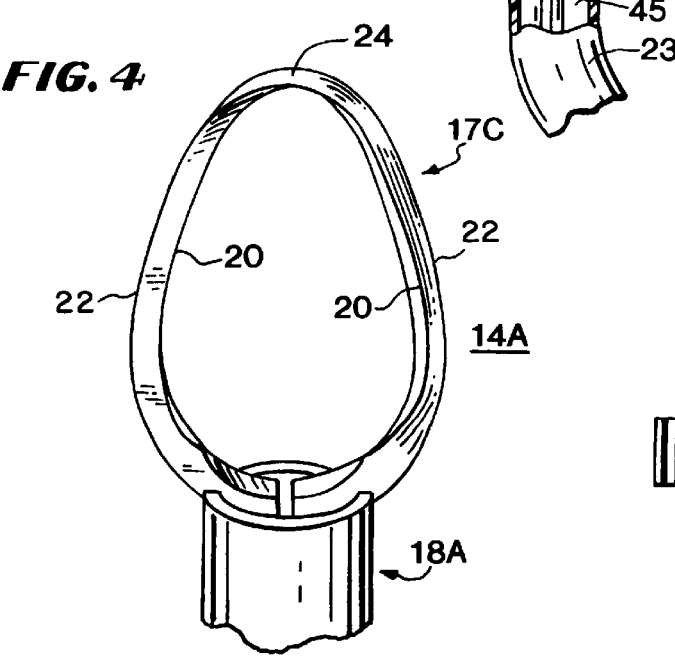
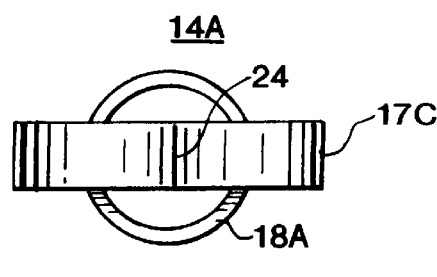
FIG. 3
FIG. 4
FIG. 5

REMOVAL OF TISSUE

This application is a divisional of U.S. application Ser. No. 08/828,928 filed Mar. 28, 1997 now U.S. Pat No. 5,911,699, which is a continuation-in-part of U.S. application Ser. No. 08/625,909 filed Apr. 1, 1996, now U.S. Pat. No. 5,722,945, which is a continuation-in-part of U.S application Ser. No. 08/372,866 filed Jan. 13, 1995, now abandoned, which is a continuation of U.S. application Ser. No. 08/035,985 filed Mar. 22, 1993, now abandoned, which is a continuation-in-part of U.S application Ser. No. 07/759,937 filed Sep. 16, 1991, which is a continuation of U.S. application Ser. No. 07/680,292 filed Apr. 4, 1991, now abandoned, which is a continuation-in-part of U.S. application Ser. No. 07/553,975 filed in the name of Aziz Y. Anis on Jul. 17, 1990, now U.S. Pat. No. 5,222,959 for REMOVAL OF TISSUE.

BACKGROUND OF THE INVENTION

This invention relates to the removal of tissue from the body such as for example removal of cataracts from the eye.

It is known to remove diseased tissue from the body by fragmenting, crushing or otherwise making the tissue flowable while i n the body and then aspirating it. In one known class of surgical techniques of this type specifically intended for the removal of cataracts: (1) an incision is made along the superior corneal margin from about 10 to 2 o'clock (12 o'clock is the location closest t o the top of the head of the patient) approximately 10 mm in chord length; (2) an incision is made in the capsular wall; and (3) the cataract is removed. The anterior chamber is maintained substantially formed during the operation by means of a continuous inflow of irrigating solution.

In one prior art technique of this class for removing a cataract, the nucleus is expressed out of the eye and the cortex is removed by a process of irrigation and aspiration. In another prior art technique of this class for removing the cataract, the nucleus is removed with a vectis and about 0.1 milliliter of viscoelastic compound or irrigating fluid is introduced into the capsular bag to separate the capsular walls. With the capsular walls separated, a wedge of the cortex is engaged in the aspiration port of a cannula and peeled toward the center and then aspirated to remove it. This process is repeated so that the layers of the cortex are peeled and then aspirated inwardly through the cannula, layer by layer, until the intact capsular bag (except for the horizontal incision) is completely empty and clean.

This technique of removing the cataract is disclosed by Anis, Aziz Y., "Illustrated Step-by-Step Description of the Anis Dry Extra Capsular Cataract Extraction Technique With In-the-Bag Lens Implementation"; *Seminars in Opthalmology*, v. 1, N. 2 (June), 1986, pp. 113–129 and the technique is compared with other such techniques of this class.

Two prior art types of instruments which aid in the fragmentation and aspiration of the lens nucleus to permit extraction through a small incision are disclosed in U.S. Pat. No. 3,589,363 to Anton Banko et al.; U.S. Pat. No. 3,902,495 to Steven N. Weiss; U.S. Pat. No. 3,693,613 to Charles Kelman et al.; and U.S. Pat. No. 4,041,947 to Steven N. Weiss et al. This instrument is intended in the prior art to fragment a lens nucleus using ultrasonic vibrations to aid the irrigation/aspiration of the lens. The ultrasonic vibrations laterally reciprocate the tip of an instrument to fracture the cataract after which it can be aspirated.

A further type of instrument is disclosed in U.S. Pat. No. 4,908,015 issued to Anis on Mar. 13, 1990. This patent describes an instrument which rotates a solid member having blades extending from it to grind the lens.

These tissue removal techniques have several disadvantages, such as: (1) they risk tearing the capsular wall with the reciprocating ultrasonic vibration tools or with the rotating blades; (2) under some circumstances, they require large incisions in or removal of parts of the capsular wall; and (3) they may require the use of several different instruments.

Still another type of prior art technique for removing cataracts is disclosed in U.S. Pat. No. 3,996,935 to Banko issued Dec. 14, 1976. This type of instrument shows cooperating jaw-like members, one of which rotates inside the other to break up the lens by shearing sections of it. It aspirates fragments through the instrument. This type of instrument has a disadvantage in that it can break the capsular wall and is relatively complex. Part of the disadvantage comes from the teaching that it may be rotated manually or mechanically without a corresponding teaching of the rate of rotation required for efficient use.

Still another prior art instrument includes a small rotary magnetic cutter that is injected through the capsular wall and a means for applying magnetic fields that control the magnetic cutter in position. The small magnetic cutter is rotated as it moves from position to position in the capsular bag and to abrade or cut the lens that is to be removed.

This instrument has several disadvantages, such as: (1) it is relatively complicated and expensive because of the need to remotely control the small cutter; and (2) does not incorporate any mechanism for aspirating the lens particles as they are abraded from the lens.

In still another prior art device disclosed in U.S. Pat. No. 4,002,169, small retractable wires are rotated in a range of 5 rpm to 16,000 rpm. There is no teaching of selecting the speed for surface discrimination and the device relies on blunt surfaces to avoid damage to the capsular wall instead. This device has the disadvantages of: (1) providing a relatively slow cutting velocity range with blades not shaped for cavitation or turbulence; (2) not providing a range of velocities sufficient to form small particles that can be aspirated through a small hole; and (3) not providing for aspiration during fragmenting, thus blocking visibility with particles.

Each of these prior art type s of instruments includes a handpiece and a console. The handpiece is held by the surgeon and includes an operative tip that, at one point in time, enters the capsular sac to fragment and remove the cataract. The console includes controls for the handpiece such as those that control the direction of movement and speed of movement of the tip, rate of flow of liquids, the suction or aspiration pressure and the drivers that apply power to the handpiece at the appropriate values. Generally, the consoles are designed together with a particular type of handpiece used in a specialized technique of ocular surgery.

A still further type of instrument is disclosed in U.S. Pat. No. 4,504,264 to Kelman issued Mar. 12, 1985. This patent discloses an instrument that reciprocates a cutting tip ultrasonically and oscillates it rotationally about its longitudinal axis at a rate of one hertz through an angle of between five degrees to 60 degrees. Because of dwell time at each change of rotational direction and speed limitations inherent in the direction changes, this instrument does not provide the advantage of breaking the tissue into particles so small as to not cause plugging nor impede visibility of the instrument tip.

The prior art arrangement has several disadvantages, such as for example: (1) it is difficult for the surgeon to use the most modern techniques without investing substantial amounts of money in purchasing additional consoles for the newer instruments; (2) for each new handpiece designed for a particular technique, the surgeon must adapt to different controls in the console itself rather than relying upon controls with which he is already familiar; (3) the handpieces are subject to causing plugging, poor visibility into the eye and excessive pressure on the capsular wall from movement of large particles; and (4) different equipment is necessary to remove vitreous liquids.

SUMMARY OF THE INVENTION

Accordingly, it is an object of the invention to provide a novel technique for tissue removal.

It is a further object of the invention to provide a novel instrument for fragmenting and removing a cataract during cataract removal surgery with low risk of damage to the capsular wall.

It is a still further object of the invention to provide a novel instrument designed to fragment tissue without damage to the nearby tissue such as for example not damaging the capsular wall while removing the lens during cataract removal surgery or not damaging artery or vein walls while removing cancerous tissue near the vein or artery.

It is a still further object of the invention to provide a novel instrument and method for removing tissue that powders the tissue and aspirates it while maintaining good visibility.

It is a still further object of the invention to provide a novel interface that permits the connection of a phacotmesis handpiece to consoles designed specifically for other ocular surgery such as consoles designed originally to cooperate with a phacoemulsification handpiece.

It is a still further object of the invention to provide an instrument capable of vitrectomy and removal of cateracts with the same handpiece.

In accordance with the above and further objects of the invention, an incision is made for the insertion of a surface-discriminating, fragmenting tool. The surface-discriminating, fragmenting tool fragments and permits aspiration of high mass, rough-surface, rigid tissue without damaging nearby smooth, flexible, low mass walls. The tool fragments some tissue but avoids fragmenting other tissue by discriminating between tissues. This discrimination is based on one or more of several factors including: (1) the rigidity of the tissue; (2) the amount of mass of the tissue; (3) the angle of the tissue to the direction of movement of the tool; (4) the roughness of the surface of the tissue; and (5) the size and shape of the surface of the tissue to the extent the size and shape affect the tendency of the negative pressure created by aspiration and/or irrigation to move the tissue toward the surface-discriminating, fragmenting tool.

The surface discrimination of the tool is controlled by moving surfaces which fragment diseased tissue on impact, referred to as phacotmesis, and cause cavitation forces that further fragment and mix fragments of tissue, referred to as phacocoelosis, but which move at a rate of speed slow enough so that the more integrated, more flexible, lower mass and smoother tissue is moved away without fragmenting. The tissue is not constrained by opposed shear forces of the tool as in some prior art rotating tools nor is the higher mass, rigid tissue moved significantly as a bulk.

The surfaces of the instrument fragment tissue that: (1) is stiffer and has a higher modulus of rigidity; and (2) is at an angle to the cutting edge closer to 90 degrees and receives less force moving it away. Thus, the surgeon removing a cataract adjusts the speed of movement of the tool surfaces, the aspirating and irrigation forces, the rake angle of the tip and the cavitation level as controlled by the position of the tool surface, the velocity and the shape of the moving surface. The adjustment is made to fragment the cortex because of its higher mass, modulus of elasticity and projections in the path of the tool surfaces but to move the capsular wall because of its lower mass, lower modulus and fewer projections closer to 90 degrees and not fragment it.

In one embodiment, a moving, fragmenting surface moves at an angle with the normal to a cataract surface, which angle is obtuse and generally close to being perpendicular to the normal in such a manner as to mix particles and to cause or aid ultrasonic motion normal to the tissue in causing cavitation and in fragmenting and mixing the cataract particles while maintaining the direct force on the cataract that could accelerate tissue against the capsular wall relatively low. In a preferred embodiment, the fragmenting surface is moved ultrasonically along the normal while it is moving at an angle to the normal such as by rotating continuously at least through several 360 degree rotations in one direction.

The aspiration pressure is more effective within the moving surfaces of the rotating tip. It is low enough to pull the fragmented tissue and tissue to be fragmented but it does not hold the smooth flexible capsular wall against movement away from the moving surfaces of the tool. The rotating surfaces move the smooth wall outwardly and provide some counter pressure to the aspirating pressure inside the fragmenting zone. The vibrating speed and rotational speed can be adjusted to powder the cateract so as to maintain good visibility and ease of aspiration and can be adjusted for vitrectomy.

In the case of cataract removal surgery, a small incision of two to seven millimeters and preferably three millimeters is made in the sclera along the corneal border at 12 o'clock and another incision of similar dimension or a round hole is made in the anterior capsular wall. The instrument is inserted and fragments the lens matter without fragmenting the capsular wall. The factors useful in surface-discriminatory, fragmenting differ from eye to eye or tissue to tissue and may be selected in accordance with the surgeon's observations. These factors are the speed of the moving surfaces with respect to the tissue, the holding pressure from aspirating vacuum and irrigating liquid, the location and position of the moving surfaces, the rake angle of the cutting edge of the moving surfaces and the shape of the portions of the moving surfaces most related to cavitation. These factors are established by the surgeon as a function of the mass of the capsular wall and the mass of the tissue to be fragmented, the stiffness and smoothness of the capsular wall or other healthy smooth tissue and the hardness and flexibility of the tissue.

In one embodiment, moving surfaces of the fragmenting tool hit the cells at a substantially tangential angle and distort them or cut them with their leading edges while the trailing edges create cavitation that further breaks and mixes the tissue without imparting such force to the tissue in a direction that may injure the capsular wall. For large and rigid or for rough surfaces, the shear force and cavitation is sufficient for fragmentation whereas for more flexible, lower mass and smoother surfaces, the leading edges and the cavitation tend to move the surface away and thus avoid fragmentation. The aspirating port or ports tend to pull the fragmented material into the interior of the tool.

In a preferred embodiment, a tubular member has a central, aspirating channel along its longitudinal axis with one end having a fragmenting tip and the other end being adapted to rotate the tube. In one embodiment, the cavitation is at low frequency below the ultrasonic frequency range. In a preferred embodiment, the tip is rotated continuously in one direction for more than one 360 degree cycle and at the same time ultrasonically reciprocated.

As can be understood from the above description, the technique and instrument of this invention have several advantages, such as: (1) they selectively fragment some tissue without damaging other nearby tissue; (2) they are able to fragment, mix and aspirate tissue, and in the case of cataract removal, while maintaining good visibility; and (3) the same handpiece can perform vitrectomy.

SUMMARY OF THE DRAWINGS

The above noted and other features of the invention will be better understood from the following detailed description when considered with reference to the accompanying drawings, in which:

FIG. 3 is a fragmentary sectional view of another portion of the embodiment of FIG. 1;

FIG. 4 is a fragmentary, perspective view of another embodiment of blade portion usable as a replacement for the blade portion in the embodiment of FIG. 1;

FIG. 5 is a plan view of the embodiment of FIG. 4;

DETAILED DESCRIPTION

Figure 1:
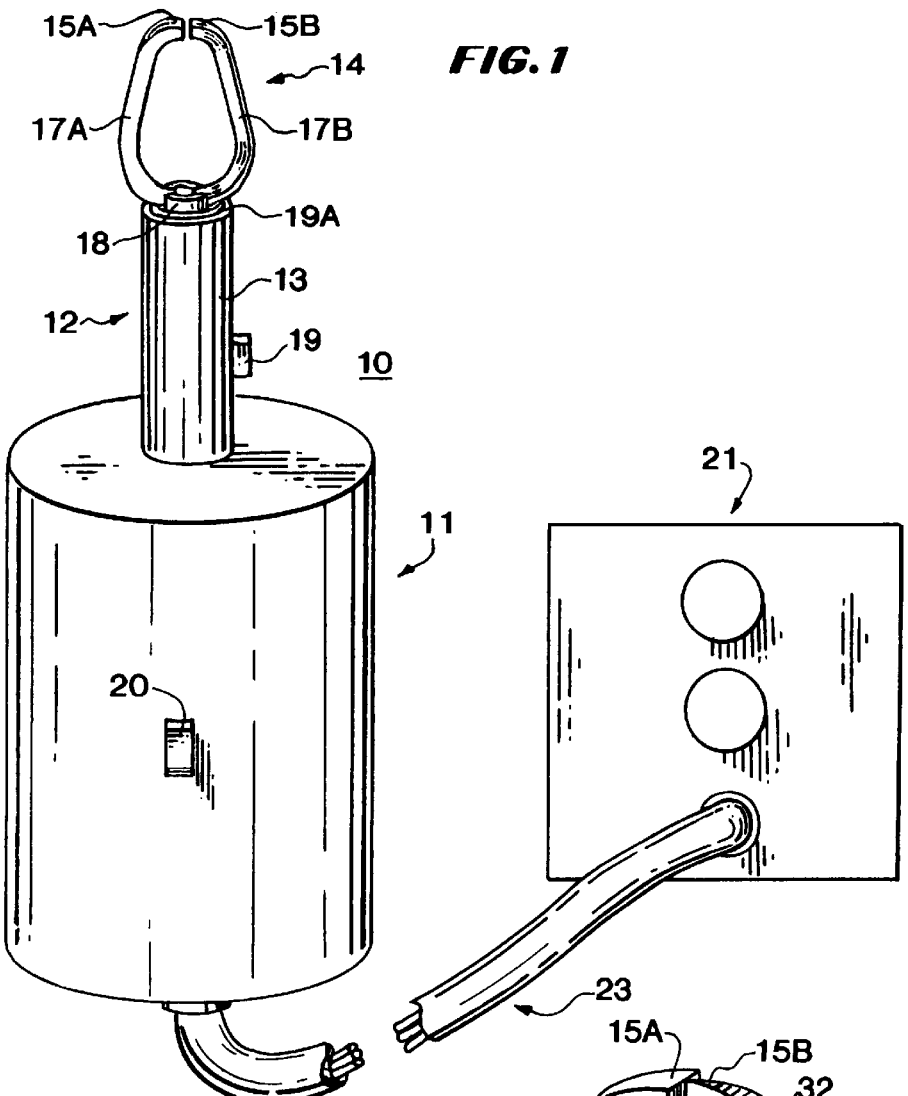
FIG. 1 is a simplified, elevational view of a handpiece and control console for fragmenting and removing cataracts in accordance with an embodiment of the invention.

In FIG. 1, there is shown an elevational view of a surface-discriminating, fragmenting handpiece 10, connecting tubing 23 and a console 21. The handpiece 10 includes a drive portion 11, a blade portion 14 and a tubular sleeve portion 12. The tubular sleeve portion 12 includes a tubular casing 13 and an inner tubular aspirating drive shaft or sleeve 18. The drive portion 11 houses the motor, an on-off switch 20 and connectors for irrigating fluid and aspirating vacuum pressure.

The blade portion 14 includes blades 17A and 17B each of which is fastened to the rotatable tubular shaft 18 at diametrically opposite locations on the shaft 18 and each of which has a corresponding one of blunt tips 15A and 15B turned inwardly to avoid cutting. The outer tubular casing 13 includes within it a movable sleeve 19A so that upon longitudinal movement of a button 19 with respect to the outer casing 13 of the tubular sleeve portion 12, the blades 17A and 17B move apart in a fragmenting position in response to one direction of movement of the button 19 and are forced within the movable sleeve 19A within the tubular sleeve portion 12 against the pressure of the spring-like blades 17A and 17B upon movement in the other direction of the button 19 to fit within a smaller incision such as a 2 millimeter opening. The blades 17A and 17B are narrower in the direction of rotation and blunt on the trailing edge to cause cavitation.

With this arrangement, the blades 17A and 17B may be moved together for insertion of the handpiece 10 into a capsular sac through a relatively small aperture and then permitted to expand outwardly so that upon rotation of the blade portion 14, the cortex and nucleus are fragmented within the capsular sac. In the embodiment of FIG. 1, the handpiece 10 includes a motor for rotating the shaft and a connecting tubing 23 for aspirating fragments. The console 21 may include for cooperation with the handpiece 10, a standard source of electrical power, a vacuum source, a source of irrigating liquid and a pump for irrigating liquid. These elements are conventional and are not part of the invention except insofar as they cooperate with the handpiece 10.

Figure 2:
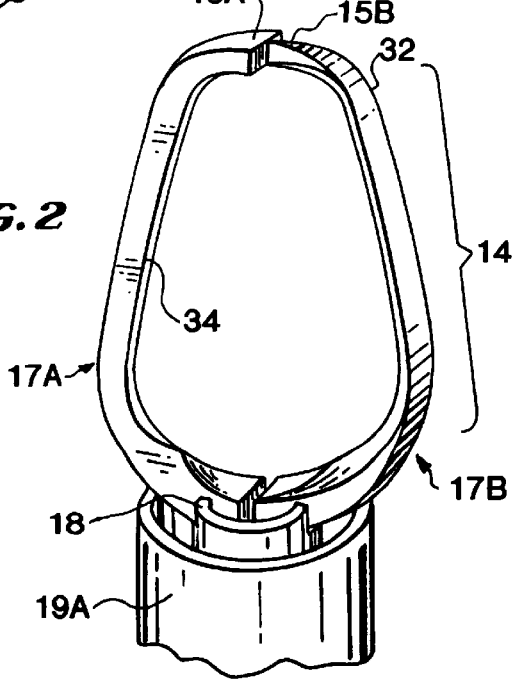
FIG. 2 is an enlarged, perspective view of a portion of the embodiment of FIG. 1.

In FIG. 2, there is shown an enlarged, fragmentary perspective view of the blade portion 14 of the tool assembly having first and second blades 17A and 17B with corresponding blunt ends 15A and 15B. The blades 17A and 17B are sufficiently flexible in the embodiment of FIG. 2 to expand until they form outwardly, curved, cutting surfaces extending beyond the surfaces of the outer casing or shaft 13 (FIG. 1) and have sharpened edges 32 and 34 tangentially to or pointing inwardly from the circles of rotation formed as they rotate. When the blades 17A and 17B are pulled inwardly by movement of the sleeve 19A upwardly, they fit within a cylinder having a diameter of less than two millimeters.

While the embodiment of FIGS. 1 and 2 have blades with sharpened edges pointing tangentially to or inwardly from the direction of rotation, sharpened edges are not necessary and the angle of attack or rake angle of the sharpened edges may vary. However, the angle of attack may be tangential to the path of rotation or any larger or smaller angle. For this purpose, any one of several multiple blade portions 14 with their attached inner drive shaft 18 may be inserted into the sleeve portion 12 and drive portion 11. The blade portion is selected by the physician and one fact in such selection is the angle of attack of the blades.

To permit compressing of the blades 17A and 17B into a protective sleeve, the tubular sleeve portion 12 includes the three coaxial sleeves 18, 19A and 13 (FIG. 1) in that order outwardly from the central axis. The blades 17A and 17B are mounted to the inner tubular drive sleeve 18 for rotation therewith and there is a space between the sleeves 18 and 19A for irrigating fluid to flow. The movable sleeve 19A is affixed to the button 19 (FIG. 1) and is movable axially with respect to inner drive sleeve 13 to engage the blades 17A and 17B and to compress them inwardly.

In FIG. 3, there is shown a fragmentary longitudinal sectional view of the tubular sleeve portion 12 and the drive portion 11: (1) having within the sleeve portion 12, the inner rotatable tubular aspirating drive shaft or sleeve 18, the movable tubular protective sleeve 19A and the outer sleeve 13; and (2) having within the drive portion 11, a motor 40 for rotating the inner aspirating drive shaft 18 to turn the blades 17A and 17B (FIG. 1), a hollow aspirating tube 27 to apply vacuum pressure to the interior of the inner shaft 18, an irrigating tube 17 communicating with the movable sleeve 19A to apply irrigating fluid through the sleeve 19A and through electrical wires 25 to control the motor 40. The inner shaft 18 is coupled at one end 42 to the output shaft 44 of the motor 40 for rotation therewith and to a tubular connection 45 for aspiration.

As shown in this view, the outer sleeve 13 supports within it the movable sleeve 19A with the button 19 extending through a slot in the outer sleeve 13 by which the movable sleeve 19A may be moved upwardly and downwardly to bend the blades 17A and 17B inwardly for retraction or to permit them to expand outwardly in the cutting position to their normal position for rotating and in some embodiments still further under centifugal force when rotating. However, the moment of inertia of the blades 17A and 17B is sufficient so that the centrifugal force does not force the points to point outwardly and only the bent flat surface is presented to the outer sleeve 13 during rotation. It is spaced from the movable tube 19A to permit irrigating fluid to flow therebetween and contains in its center, an opening 15 which extends downwardly for aspiration of tissues.

To provide irrigating fluids, the irrigating tube 17 is connected through a cable 23 to the console 21 (FIG. 1) from which irrigating liquid is pumped through the tube 17 around the motor 40 and to the space between the movable tube 19A and the inner shaft 18 to supply irrigating fluid to the capsular sac. To aspirate tissue, the central opening 15 in the inner shaft 18 passes through an opening 29 in the wall of the inner shaft 18 and communicates through a sealed circular ring 31 with the aspirating conduit 25. The connection 45 passes around the motor 40 and through the cable 23 to the console 21 (FIG. 1) which applies slight negative pressure to aspirate tissue. The cable 23 also carries electrical conductors for the motor 40 which are connected in series between the switch 20, and a source of electrical power in the console 21 and the motor 40.

To use the embodiment of FIGS. 1–3, an incision is made for the insertion of the surface-discriminating, fragmenting handpiece 10. The surface-discriminating, fragmenting handpiece 10 fragments and permits aspiration of the tissue but avoids damaging nearby smooth, flexible walls. Instead, it fragments rougher, more rigid surfaces of higher masses. This surface discrimination is controlled by the moving surface of the blades 17A and 17B, which permit the diseased tissue to be strained or cut by the blades 17A and 17B and further fragmented by the forces of cavitation within their fragmenting zone but which move at a rate of speed and have openings between them of such a size that the more integrated, lower mass or more flexible and smoother tissue does not fall within their fragmenting zone but is moved away from the moving surfaces. The aspirating pressure, cavitation and turbulence is counteracted or attenuated within the sphere of the rotating ring to avoid damage to the flat surface tissue.

In the case of cataract removal surgery, a small incision of two to seven millimeters and preferably three millimeters is made in the schlera along the corneal border at 12 o'clock and another incision of similar dimensions is made in the capsular wall. The instrument is inserted and fragments the higher mass, more rigid, rougher lens without fragmenting the capsular wall.

The actual time that the fragmenting zone must be open to fragment diseased tissue without injuring smooth walls differs from eye to eye or tissue to tissue and may be selected in accordance with the surgeon's observations prior to use. It is a function of: (1) the rigidity of the tissue; (2) the mass of the tissue; (3) the angle of the tissue to the direction of movement of the tool; (4) the roughness of the surface; and (5) the effect of the negative pressure pulling the tissue inwardly such as the aspiration vacuum pressure which may vary in its effect depending on the size and shape of the tissue.

The surface discrimination of the tool is controlled by moving surfaces which cause the diseased tissue to fragment under impact, referred to as phacotmesis, and cavitation forces, referred to as phacocoelosis, but which move at a rate of speed slow enough so that the more integrated, more flexible, lower mass and smoother tissue is moved away without fragmenting. The surfaces of the instrument fragment tissue that: (1) is stiff; (2) has a high mass and large inertia; and (3) is at an angle to the cutting edge close to 90 degrees.

To take advantage of the differences between the tissue to be fragmented and the lower, more flexible tissue, the surgeon removing a cataract adjusts the speed of movement of the tool surfaces, the aspirating and irrigation rates, the rake angle of the leading edge of the blade surfaces and the cavitation level as controlled by the position of the blade surfaces, the velocity and the shape of the moving surfaces, especially the trailing edge of the blades. The adjustments are made to fragment the cortex because of its higher mass, modulus of elasticity and projections in the path of the tool surfaces and to move the capsular wall away from the blades because of its lower mass, lower modulus and fewer projections closer to 90 degrees. Tips are replaced to change the rake angle and cavitation surfaces.

The aspiration pressure is more effective within the moving surfaces of the rotating tip. It is low enough to pull the fragmented tissue and tissue to be fragmented but does not hold the smooth wall against movement nor pull it inwardly. The rotating surfaces move the smooth wall outwardly and provide some counter pressure to the aspirating pressure inside the fragmenting zone. In one embodiment, radially, inwardly, extending edges further pull and mix tissue within the fragmenting zone.

To better describe this and other embodiments, some special terminology is useful. For purposes of this description, the words, "low power" mean less than one horsepower (1.341 kilowatts). In this description, the words, "motion resistance" mean the resistance of a portion of tissue to movement when impacted by a moving tool surface caused by the inertia of the tissue and the effect of the inertia of other tissue connected to it taking into consideration the flexibility of the connecting tissue.

In this description, the words, "fragmenting velocity" mean the minimum velocity of a moving surface of a tool with respect to predetermined stationary tissue that the moving surface of the tool impacts that is sufficient to cause strain in the tissue of at least ten percent of the distance moved by the entire tissue mass and to break the tissue by combined strain, cutting and cavitation effects. This value is specific for a predetermined stationary tissue having a predetermined motion resistance. It assumes that the tool surface has sufficient kinetic energy to maintain its velocity constant in spite of the impact. The fragmenting velocity is affected by: (1) the angle the motion of the moving surface makes with the surface of the tissue; and (2) the momentum of the moving surface.

In the embodiments of FIGS. 1–3, a ring or partial ring having a diameter of two millimeters in the widest distance perpendicular to the axis of revolution forms a surface of revolution when rotated having at any one time open spaces and a solid cutting ring. The ring is rotated at approximately 120,000 rpm (revolutions per minute). The solid ring is approximately 0.50 millimeter wide along the surface of revolution, leaving an open area in the surface of slightly less than nine square millimeters and more precisely, 8.9 square millimeters with a length of 2.4 millimeters at the longest circle of a segment.

The time between portions of the solid ring sweeping across any surface of revolution is approximately every 250 microseconds and should be no longer than once every three milliseconds (1,000 rpm) but may be as short as 0.75 of a microsecond (400,000 rpm). With this arrangement and with parameters adjustable for the particular circumstance, the capsular wall does not enter into the fragmenting zone within and near the surface of revolution and is not cut and yet the ring is able to fragment the lens for easy aspiration.

In FIG. 4, there is shown a second embodiment of blade portion 14A, having a shaft 18A connected to a blade 17C formed as a partial zone of a circle or an arc extending from the shaft 18A and having a pear-shaped, blade portion 14A with: (1) blunt trailing edges 20; (2) sharpened leading edges 22; (3) a wide base attached to the shaft 18A that is narrower along the axis of the shaft 18A so that there is at the wide portion, a blunt trailing edge 20 and a sharpened leading edge 22 as the cutting blade 17C rotates about the shaft 18A; and (4) an axis of rotation along the shaft 18A between the base and the narrower upper portion. The apex is generally blunt, but in some embodiments has a drill shape at the apex 24.

It has been found that the sharpened leading edges 22 strain and elongate the cells of higher-mass, rigid material but push away flexible and low-mass material. The leading edges 22, under some circumstances, cut or scrape fine particles from the harder material that might otherwise plug the aspirating channel but the cavitation effect fragments the particles into small particles that can easily be aspirated. The blades 17C are shaped to maximize cavitation that liquifies and stresses lens matter and any viscous fluids and causes fragmentation and mixing of the higher-mass more rigid material. In the embodiment of FIG. 4, the blades have two blunt sides, a top blunt portion 24 and a blunt portion at the mounting base to the tube 18A for strength at the bottom and to form a non cutting surface at the top.

In FIG. 5, there is shown a top view of the embodiment of FIG. 4, having the blade portion 14A with the blade 17C shaped with a thicker portion having a blunting surface 24 at its upper end facing away from the direction of the tubular shaft 18A and rotating thereabout. However, in some embodiments, it has a cutting edge to permit it to provide an abrading center area in the forward direction for positioning at a point to be fragmented. This embodiment operates substantially the same as the prior embodiments except that its unique shape enables careful placement for special purposes. Instead of a cutting edge, the top portion 24 may be bent inwardly or may be blunt to avoid cutting at its top.

Figure 6:
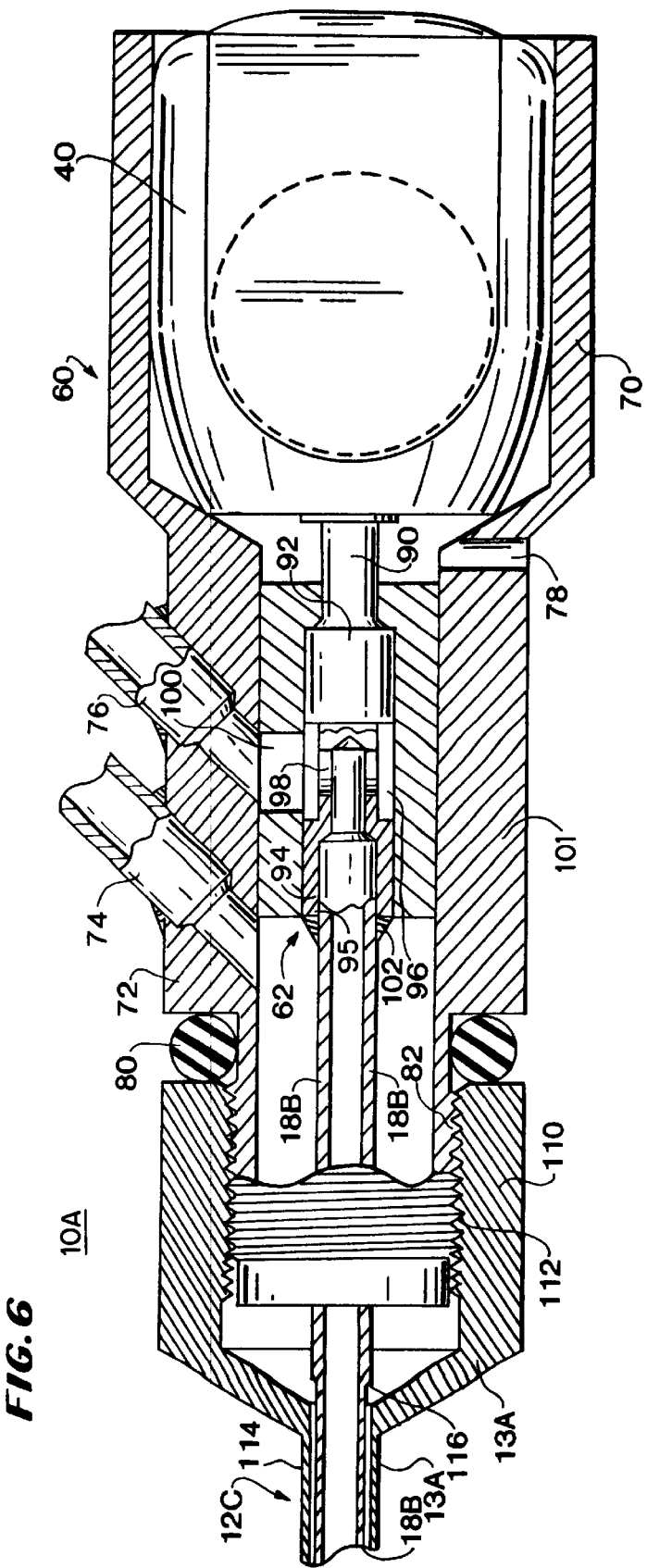
FIG. 6 is a fragmentary, elevational view, partly sectioned and partly diagramatic of another embodiment of handpiece.

In FIG. 6, there is shown a fragmentary, partly diagramatic and partly longitudinally sectioned view of another embodiment of handpiece 10A which is operated by a similar dental drill motor 40 and adapted to receive a tool by having inserted therein an aspirating drive sleeve 18B of a tubular sleeve portion 12C substantially identical to that of the embodiments of FIGS. 1–5 except that the blade portion is constructed in a different manner on the end of the inner shaft 18 (FIG. 1–3) as will be described hereinafter.

The handpiece 10A includes, in addition to the aforementioned motor 40 and the aspirating drive sleeve 18B, an outer housing 60 and a motor-tool sleeve coupling 62 with: (1) the motor 40 being connected to the drive sleeve 18B through the coupling 62 and being located within the outer housing 60; (2) the sleeve 18B extending outwardly thereof for rotation by the motor 40 through the coupling 62 during operation of the handpiece.

To enclose and provide the necessary liquid and vacuum connections to the operative tool, the outer housing 60 includes a motor housing portion 70 and a tool and coupling housing portion 72 integrally formed together with a tubular connector 74 for irrigating fluid, a tubular connector 76 for aspirating negative pressure and a hole 78 being provided through the housing 60 for venting air. The air vent port 78 is an opening extending into and communicating with the interior of the motor housing portion 70 to provide cooling to the motor 40. The irrigating fluid connector 74 is an opening communicating with the interior of the housing portion 72 to apply fluid therethrough for eventual passage through a protective sleeve 13A on the outside of the drive sleeve 18B and to the operating point in a manner to be described more fully hereinafter.

The aspirating connector 76 is adapted to receive tubing for applying negative pressure through the motor-tool sleeve coupling 62 to the interior of the drive sleeve 18B to withdraw material during use of the handpiece 10A. The forward end of the tool and coupling housing portion 72 includes external threads 82 which engage internal teeth 112 on the protective sleeve 13A and a shoulder with an O-ring 80 positioned in it so that the protective sleeve 13A can be threaded onto the outer housing 60 to enclose a portion of it sealingly and extend it through its outer end in a manner to be described hereinafter.

To connect the motor 40 to the sleeve portion 12C, the motor-tool sleeve coupling 62 includes a motor output shaft 90, a cylindrical boss 92, a cylindrical support member 94, an annular groove 96 within the support member 94, two counterbores 98 through the support member 94 at the bottom of the annular groove 96, an opening 100 communicating with the aspirating connector 76 and extending through the cylindrical support member 94, a cylindrical opening 95 sized to receive the sleeve 18B and a brazed connection 102 more firmly fastening the support member 94 to the sleeve 18B. A support 101 receives the motor shaft 90 and the boss 92 which rotate within it and are supported by it. The groove 96 communicates with the opening 100 as it rotates because of its annular shape and receives vacuum pressure which it transmits through the counterbores 98 into the sleeve 18B to create negative pressure in the working tip through this elongated sleeve.

With this arrangement, the sleeve 18B is rotated and carries vacuum pressure with it to the tip. The brazed connection 102 aids in transmitting force from the output shaft 90 to the drive sleeve 18B through the boss 92 by increasing the firmness of the connection between the drive sleeve 18B and the shaft 90.

To mount and support the drive sleeve 18B, the protective sleeve 13A in the embodiment of FIG. 6 includes a cylindrical base member 110 having internal teeth 112 adapted to engage the external teeth 82 of the housing portion 72 and is sealed against the flow of fluid therethrough by the O-rings 80 compressed between the enlarged cylinder base member 110 and the housing portion 72. A narrower outer sheath portion 114 is integrally formed with the cylindrical base member 110 and receives a cylindrical passageway formed between the inner drive sleeve 18B and its outer tubular surface to permit the flow of irrigating liquid between the outer protective sleeve 13A and the inner drive sleeve 18B into the capsular bag.

With this arrangement, the drive sleeve 18B can be rotated by the motor 40 and at the same time: (1) irrigating fluid can be applied between it and the protective outer sleeve 13A; and (2) aspirating negative pressure can be applied to pull fragments along its longitudinal axis. At its outer end, the fragmenting tip or blades are formed in a manner to be described hereinafter.

Figure 7:
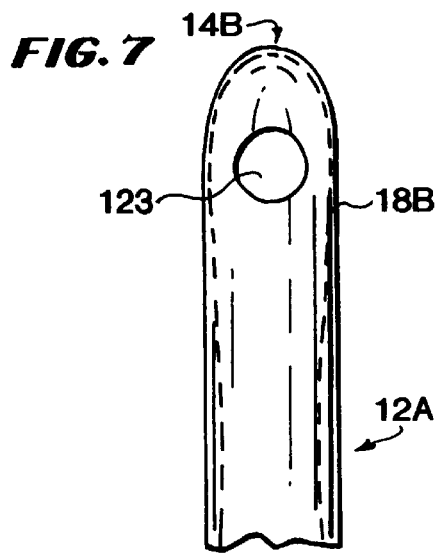
FIG. 7 is a fragmentary, elevational view of another embodiment of tool portion.
Figure 9:
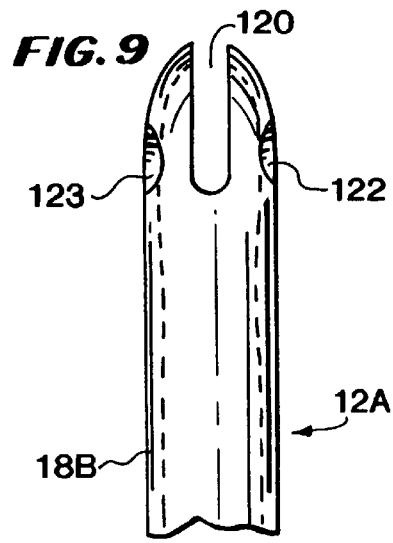
FIG. 9 is an elevational, right hand view of the embodiment of FIG. 7.
Figure 8:
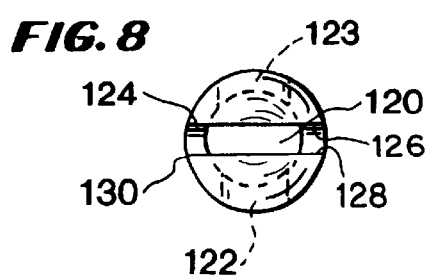
FIG. 8 is a top view of the embodiment of FIG. 7.

In FIG. 7, there is shown a front, elevational view of one embodiment of a tool having a sleeve portion 12A and a blade portion 14B with two blade members formed in its outer end and separated by an opening 123 longitudinally passing along the longitudinal axis of the tool to form the blade portion 14B at the end of the same cylinder forming the sleeve portion 12A. Both the blade portion 14A and the sleeve portion 12A are formed on a single, integrally formed cylinder that serves as an aspirating drive shaft 18B. Aspirating holes extend through the tip of the blade portion 14B orthogonal to the longitudinal axis and a slot 120 (FIGS. 8 and 9). To receive some material for aspirating, apertures 122 and 123 (FIGS. 8–10) are approximately 0.04 inch from the tip 24 (FIG. 10) of the blade portion 14B and the diameter of the aspirating drive shaft 18B is approximately 0.042 inch. The diameter of the aspirating apertures 122 and 123 are 0.018 inch and should not be larger than seven millimeters.

In FIGS. 8 and 9, there are shown a plan view and a right elevational view of the embodiment of FIG. 7, respectively, showing the slot 120 having a width of 0.008 inch and extending downwardly approximately 0.07 inch. As best shown in FIG. 8, the edges of the walls of the tube or sleeve 18B along the slot 120 have a larger or blunter trailing edge shown at 126 and a sharper leading edge shown at 124 in one embodiment as well as a blunter edge shown at 130 and a sharper edge shown at 128 so that the sharper edges 124 and 128 as the item rotates counter-clockwise as shown in FIG. 8 looking into the surface of the drawing elongate or cut the tissue within the eye and create cavitation at the blunter edges 130 and 126.

Figure 10:
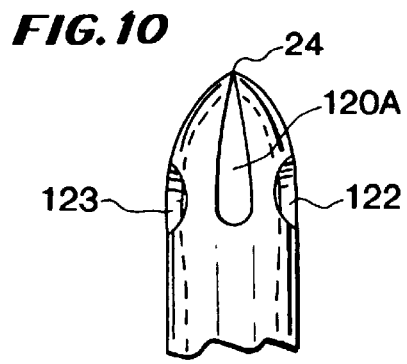
FIG. 10 is a fragmentary, elevational view of a tool tip which represents a variation of the tool tip of FIGS. 7–9.

In FIG. 10, there is shown a fragmentary, front elevational view of another embodiment showing the tip 24 along the slot 120A brought together, welded and offset to provide a sharper and a blunter edge by offsetting the edges along the slot 120A to a greater degree but without the need for changing the thickness of the tube walls. This embodiment forms a rake angle of 90 degrees and two cutting edges, but slots at three locations in the wall of sleeve 18B can also be formed instead of two slots 180 degrees apart, providing a 60 degree rake angle and three cutting edges, or four slots can be formed to provide a 45 degree rake angle and four cutting edges. Moreover, the tips can be brought together as in FIG. 10 to form a smooth protective dome or can include a cutting edge or be open. The tip can also be twisted, which will change the rake angle along the slot and provide a cyclone fan pulling effect.

Figure 11:
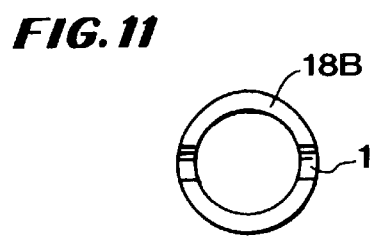
FIG. 11 is a diagramatic, top view of a tool tip illustrating a first step useful in making the embodiment of FIGS. 7–9.
Figure 12:
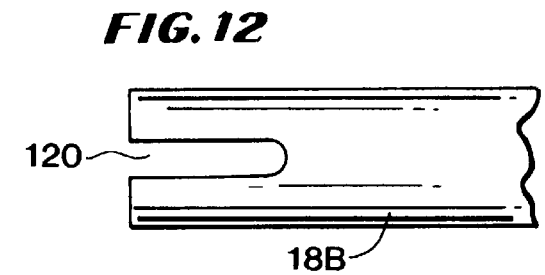
FIG. 12 is a fragmentary, elevational view of the tool tip shown in FIG. 11.
Figure 13:
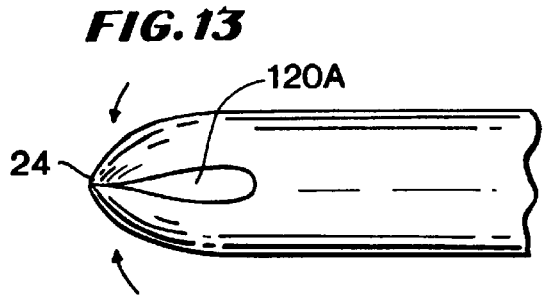
FIG. 13 is a n elevational view of a tool tip illustrating a second step in preparing the embodiment of FIGS. 7–9.
Figure 14:
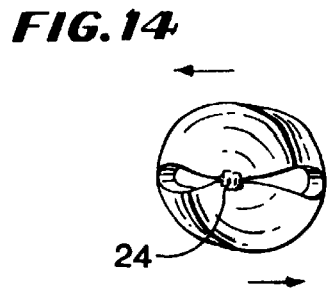
FIG. 14 is a top view of the tool tip shown in FIG. 13.

To form the embodiments of FIGS. 7–10, a tubular sleeve 18B is slotted at 120 as shown best in FIGS. 11 and 12 and pinched together. The two sides are then offset in space laterally in a direction along a plane passing through the center of the slots and the longitudinal axis of the sleeve as shown in FIGS. 13 and 14 and the tips pinched together and brazed together to form a tip such as that shown in FIG. 10. Prior to closing the tips 24, the narrower and blunter edges may be further shaped by cutting one wall at a more acute angle than the other wall and then removing the other sides of the slot with a reverse cut to form flat ends and sharpened ends.

Figure 15:
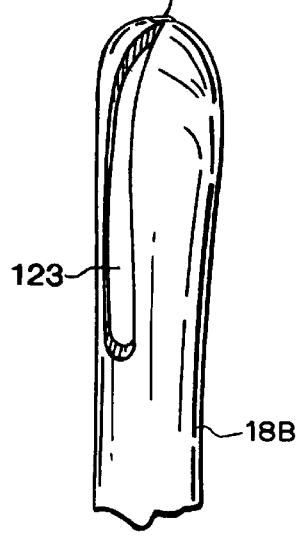
FIG. 15 is a fragmentary, perspective view illustrating an additional step in preparing the embodiment of FIGS. 7–9.
Figure 16:
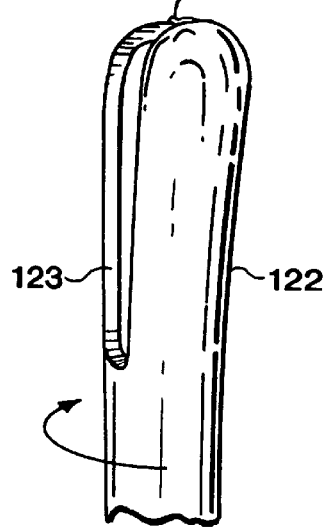
FIG. 16 is a perspective view illustrating still another possible step in preparing a tool tip similar to the embodiments of FIGS. 7–9.

To form other raking angles and/or shape the blade to pull viscous fluid, the ends are offset, twisted and brazed as shown in FIG. 15 and 16, first offset along a line or plane aligned with the two slots and longitudinal axis and then twisted at a slightly different angle to form a different rake angle and to create a cyclone pump effect. The tip is normally smooth at the very tip 24 but has a cutting effect as it moves radially outwardly.

In one version of the preferred embodiment, the tube 18B has an outer diameter of 42 thousandths (0.042) inch with two diametrically opposed slots. The ends are moved together in a curvature leaving a slot about eight thousandths inch wide at its widest point and extend from the top approximately 70 thousandths inch (70 thousandths long). Ninety degrees removed from the two slots are central aspirating apertures having a diameter of 18 thousandths of an inch and being circular in cross section. They are located with their bottom edge generally adjacent to the end of the slots.

The tube usually rotates at approximately 1600 hertz when fragmenting the nucleus in a preferred embodiment having two cutting edges and the wedged surfaces of the slots have one edge that is in a range of one thousandths of an inch to 20 thousandths of an inch thick and a trailing edge that is in the range of ten thousandths of an inch to 50 thousandths of an inch thick. Preferably, it should be in the range of 300 hertz to 4000 hertz but may be slower or faster when at a location in the capsular sac not near tissue to be preserved or which may be moved to change other tissue. The slots and rate of rotation are selected to provide, in the preferred embodiment, a surface moving 200 centimeters a second at the fastest point on the curved moving surfaces and preferably to provide a surface moving at the fastest point within a range of five meters a second to 40 centimeters per second at the fastest point but may move slower or faster under some circumstances.

Since it is a rotating surface which curves inwardly toward the center, the speed is very low at the center and, under some circumstances, does little fragmenting at the center and more and more fragmenting as the rotating radius increases to the sleeve radius. The slot is next to tissue for a very short time such as between 10 milliseconds and 1 millisecond. Each cutting edge sweeps past a point about once every 625 microseconds, preferably, or in the normal range of once every 3 milliseconds to once every 400 microseconds.

In addition to zones of a sphere and sections of a cylinder intended for use within an eye, other shapes of moving surfaces may be used and the tool has uses other than for cataract removal, such as in vascular operations. For example, multiple zones of a sphere may be spaced from each other at a shorter distance so that the item need not be rotated as fast and motion other than rotational motion may be used to prevent entrance of the tissue into the fragmenting zone. A convenient embodiment for removing structures around veins or arteries during vascular operations is dumbbell shaped so that a recess fits around the vein while spherical cutting zones are positioned on either side of the vein.

In some embodiments, the moving surface is formed of a curved member attached to a rotatable shaft having a sharpened edge at an angle of between 0 and 60 degrees but preferably 45 degrees with a surface of revolution, which surface has a center of rotation aligned with the rotating shaft. The sharpened edge of the curved member may face away from the center of rotation so that the cutting action of the sharpened surface is into the cortex and core material of a cataract.

Figure 17:
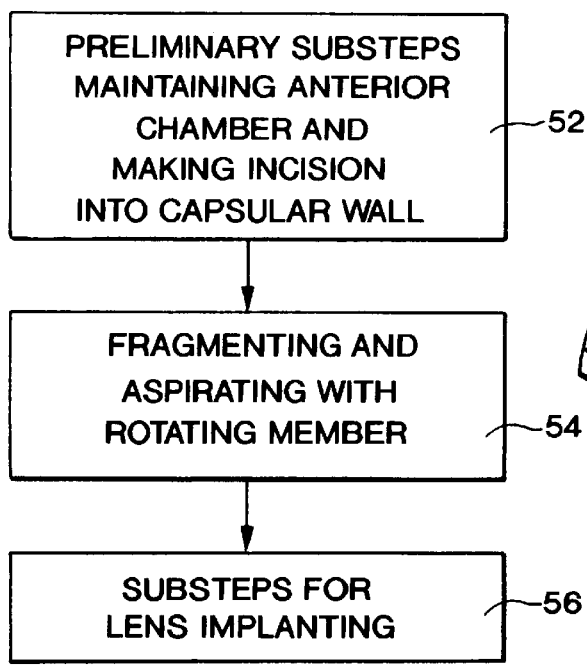
FIG. 17 is a block diagram of a process for using the instrument of FIGS. 1–6 to remove a cataract.

In FIG. 17, there is shown a block diagram generally illustrating the steps in a cataract extraction and lens implantation technique 50 comprising: (1) the step 52 which includes the preliminary substeps of maintaining the anterior chamber and making the incision into the capsular wall; (2) the step 54 of removing the lens by fragmenting it and aspirating it with the rotating member; and (3) the step 56 which includes the substeps necessary for implanting the lens.

In performing this technique, the step 52 which includes the substeps required to make the incision and maintain the anterior chamber and the step 56, which includes the substeps necessary for implanting the lens are not by themselves new and many of the steps are described in Anis, Aziz Y., "Illustrated Step-by-Step Description of the Anis Dry Extra Capsular Cataract Extraction Technique With In-the-Bag Lens Implementation", *Seminars in Opthalmology*, v. 1, N. 2 (June), 1986, pp. 113–129. Moreover, the removal of the lens may not be followed by implantation but may be part of a treatment in which the aphakia is treated by contact lens or glasses.

The step 54 of removing the lens by fragmenting and aspirating it with the rotating member includes: (1) the step of inserting the handpiece; (2) the step of breaking and removing the hardened part of the nucleus; and (3) the step of aspirating particles of tissue. These steps are all performed through a small incision while the anterior chamber is maintained with a viscoelastic medium. Hydrodelineation may be performed as described in U.S. Pat. No. 4,908,015, if desired, but such hydrodelineation is not part of this invention. If necessary, vitreous fluids may be aspirated.

The step 52 which includes preliminary substeps of maintaining the anterior chamber and making the incision in the capsular wall includes the substep of making a small incision in the capsular bag, preferably no greater than three millimeters in length and in the range of one to two millimeters. This incision is made while the anterior chamber is maintained and is made as small as possible to maintain the structure of the capsular bag to the extent possible. Through this small incision, the step 54 of fragmenting and aspirating and the step 56 of implanting a lens are performed. Under some circumstances, the incision may be four or five millimeters but should always be less than 7 millimeters.

Figure 18:
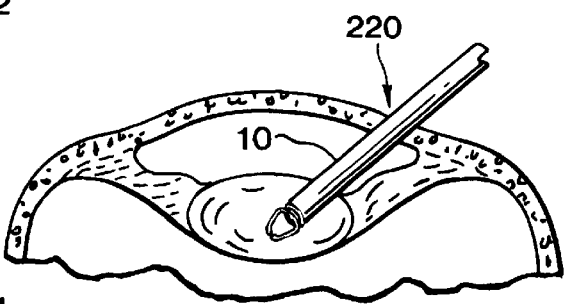
FIG. 18 is a simplified, cross-sectional view of an eye and cataract removal handpiece tip illustrating a portion of the technique of this invention.

With the posterior capsule in focus in the focal plane of the microscope, the handpiece 10 is introduced through an incision shown at 220 in FIG. 18 in the wall of the capsular sac. The tip of a handpiece 10 is thrust through the incision in the wall of the capsular bag and into the lens therein.

The tip is rapidly rotated and linearly vibrated in a direction normal to the plane of rotation while slight negative pressure is applied to aspirate the fragments. The rotating tip is inserted gradually into the cortex and nucleus and, from time to time, a small amount of irrigating fluid is injected. Fragmented cortex or nucleus material is aspirated. The speed of rotation and vibration can cause the particles to be so fine as to be substantially invisible and not to interfere with visibility of the surgery. The rotation and aspiration mix the small particles and easily pull them into the instrument. The same handpiece can be used to remove vitreous fluids. After removal of the cataract and the handpiece with the capsular sac relatively intact, a lens implant is inserted through a relatively small opening as described in the above publication of Anis.

Generally, the nucleus is first removed then the cortex. The surface-discriminating, fragmenting handpiece fragments and permits aspiration of the cotex and nucleus without damaging nearby smooth walls of the capsular sac. It avoids fragmenting the smooth walls with its cutting edges but fragments rougher, stiffer higher-mass tissue, moving it into a negative pressure zone for aspiration. The smooth more flexible, lower mass surfaces are moved by the blades which hit it at an angle. The tissue being fragmented is hit at an angle and is subject to cavitation rapidly and repeatedly with a force each time that does not move the entire material to the extent that it may damage the capsular wall or other healthy tissue that is not to be fragmented but does fragment the cortex.

The surface discrimination of the instrument is controlled by moving surfaces which permit the diseased higher-mass tissue to be fragmented but which move at a rate of speed and have openings between them of such a size that the more integrated flexible, lower-mass and smoother tissue does not fall within their fragmenting zone. The tissue is not constrained by opposed shear forces of the instrument but are free to move and the cutting edge of the instrument cuts tissue that: (1) is stiffer and has a higher modulus of rigidity; and (2) is at an angle to the cutting edge closer to 90 degrees and receives less force moving it away.

Thus, the surgeon removing a cataract adjusts the speed of movement of the cutting edge to cut cortex with a higher-mass and modulus and more projections in the path of the cutting surface and not the capsular wall with a lower modulus and mass and fewer projections closer to 90 degrees so it is more readily moved away from the cutting edge. The aspirating pressure is low enough to pull the fragmented tissue but not the smooth wall. The rotating surfaces move the smooth wall outwardly and provide some counter pressure to the aspirating pressure inside the cutting zone.

In using this instrument, as the lens is reduced in mass and freed from its connection to the structure of the eye by fragmentation, its tendency to move away from the cutting edges is increased. One way of compensating for this effect may be by changing the speed, the location and the direction in which the cutting edges impact the lens sufficiently often to neutralize the tendency of the impact to move the lens in one direction. Another aid is to rotate the tip to mix the particles with fluid and pull the fluid and particles into the instrument. This is done by continuously rotating the tip in one direction while ultrasonically vibrating it. Continuous rotation in one direction means rotation in one direction for more than one 360 degree cycle of rotation. Without such rapid impact, the impacting may cause the lens to move, such as by causing rotation of the lens.

Figure 19:
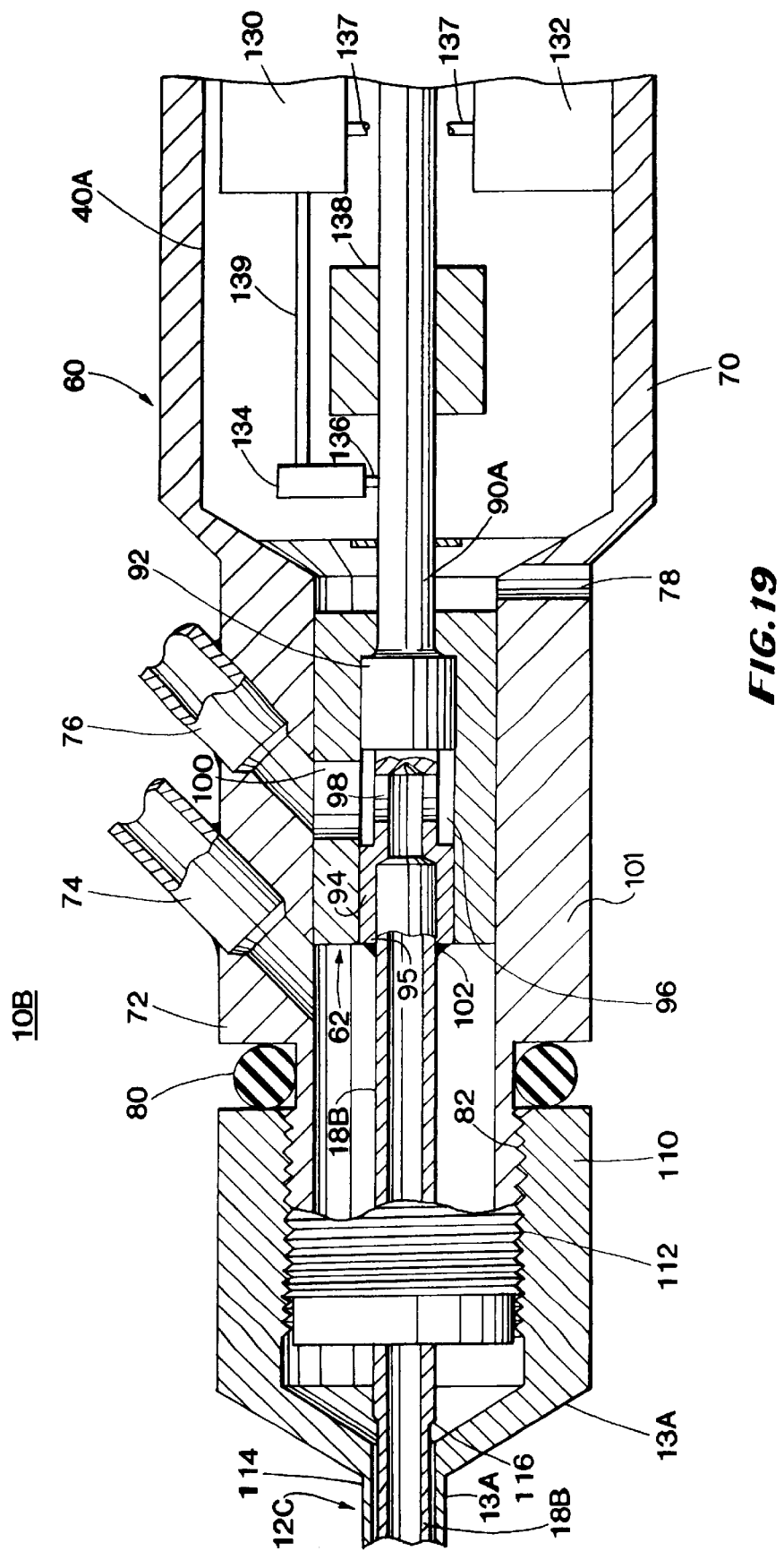
FIG. 19 is a fragmentary, elevational view, partly sectioned and partly diagramatic of still another embodiment of handpiece.

In FIG. 19, there is shown a fragmentary, partly diagramatic and partly longitudinally sectioned view of still another embodiment of handpiece 10B especially useful after the lens has been reduced in size. Instead of being operated by a dental drill motor 40, it is driven by a vibrator 40A, which may be any conventional type of vibrator such as those used to operate the tip in the above-mentioned U.S. Pat. Nos. 3,589,363 to Anton Banko, et al., U.S. Pat. No. 3,902,495 to Steven N. Weiss, U.S. Pat. No. 3,693,613 to Charles Kelman, et al, and U.S. Pat. No. 4,041,947 to Steven N. Weiss, et al. Except for the drive mechanism, the handpiece 10B is identical to the embodiment of FIG. 6 and the reference numbers for identical parts remain the same.

The handpiece 10B includes, in addition to the aforementioned vibrator 40A, an aspirating drive sleeve 18B, an outer housing 60 and a motor-tool sleeve coupling 62 with: (1) the vibrator 40A being connected to the drive sleeve 18B through the coupling 62 and being located within the outer housing 60; (2) the sleeve 18B extending outwardly thereof for vibrating curvalinear motion by the vibrator 40A through the coupling 62 during operation of the handpiece 10B.

The vibrator 40A includes a conventional oscillator 130, a source of dc power 132, and a piezoelectric or electromagnetic vibrator 134 electrically connected in series with the switch 20 (FIG. 1) to be energized and vibrate the cutting edges (not shown in FIG. 19) connected to the sleeve portion 12C as explained in connection with the embodiment of FIG. 6. A shaft 90A is mounted for rotation in bearings 138 and includes a welded arm extending orthogonally and radially therefrom, biased into contact with or fastened to a movable portion of the vibrator 134 so that vibration of the vibrator imparts rotating motion to the shaft 90A.

To connect the vibrator 40A to the sleeve portion 12C, the motor-tool sleeve coupling 62 includes the vibrator output shaft 90A, a cylindrical boss 92, a cylindrical support member 94, an annular groove 96 within the support member 94, two counterbores 98 through the support member 94 at the bottom of the annular groove 96, an opening 100 communicating with the aspirating connector 76 and extending through the cylindrical support 94, a cylindrical opening 95 sized to receive the sleeve 18B and a brazed connection 102 more firmly fastening the support member 94 to the sleeve 18B.

The bearing support 101 receives the vibrator shaft 90A and the boss 92 which rotationally vibrate within it and are supported by it. The groove 96 communicates with the opening 100 as it moves because of its annular shape and receives vacuum pressure which it transmits through the counterbores 98 into the sleeve 18B to create negative pressure in the working tip through this elongated sleeve.

With this arrangement, closing the switch 20 (FIG. 1) connects power from the power supply 132 to the oscillator 130. The vibrator 134 then vibrates at the frequency to which the oscillator 130 has been tuned by the surgeon, which vibrator 134 being energized through conductors 139. The vibrator 134 reciprocates a lever 136 turning the shaft 18B repeatedly. This causes the lens to be impacted with the cutting edges at an angle and speed that avoids damage to the capsular wall, if it should be near, and fragments the lens.

Figure 20:
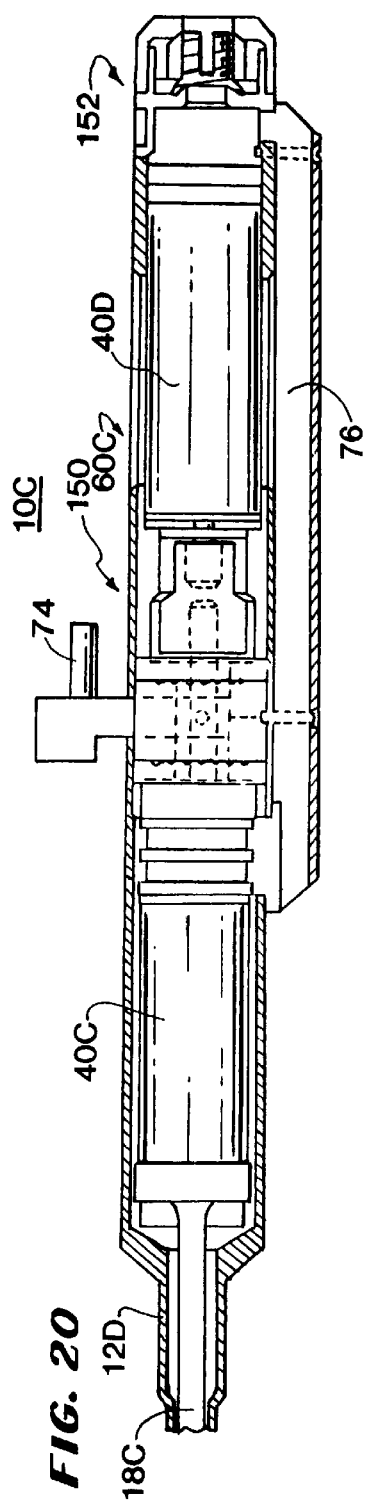
FIG. 20 is a sectional view of another embodiment of handpiece.

In FIG. 20, there is shown a partly longitudinally sectioned, fragmentary, simplified view of a handpiece 10C, having as its principal parts an ultrasonic vibrator 40C, an electrical rotational motor 40D and a aspirating tube 18C all in line with each other along a common longitudinal axis. The motor 40D is coupled to the ultrasonic vibrator 40C, which in turn is coupled to the aspirating tube 18C to impart a combined rotary and longitudinal ultrasonic reciprocating motion to the aspirating tube 18C.

With this mechanism, the aspirating tube 18C moves the fragmenting tip 14C (not shown in FIG. 20) so that it rotates rapidly, and while rotating, ultrasonically vibrates in and out of the tissue once for each small, angular increment of rotational motion, such as for example, every one degree or less. Thus, it combines the rotational movement and ultrasonic movement of prior embodiments. While the motor 40D is intended to continuously rotate the aspirating tube 18C in a single direction, such as clockwise or counterclockwise, it can alternate rotations, between clockwise and counterclockwise in the manner of the embodiment of FIG. 19. In this manner, the time of impact is primarily determined by the frequency of the ultrasonic, reciprocal motion and the location and direction are primarily controlled for a stationary handpiece by the rotational speed. By selecting the optimum or near optimum values of rotational speed and reciprocating frequency, movement of the mass of tissue with respect to fragmenting speed may be controlled.

The embodiment 10C of FIG. 20 is similar to prior embodiments in that it includes a tubular aspirating connector 76 and an irrigating connector 74 to aspirate through the center of the aspirating tube 18C and irrigate between the protective sleeve 12D and the aspirating tube 18C in the manner described in previous embodiments. In the embodiment of FIG. 20, the outer housing 60C encloses both an ultrasonic vibrator 134 (FIG. 19) adapted for reciprocally vibrating the aspirating tube 18C to which the fragmenting tip is connected in a direction aligned with the longitudinal axis of the handpiece 10B and the tip and the rotational motor 40D coupled through a coupled mechanism 150. The necessary electrical connections are supplied through an opening in a rear bulkhead 152.

Figure 21:
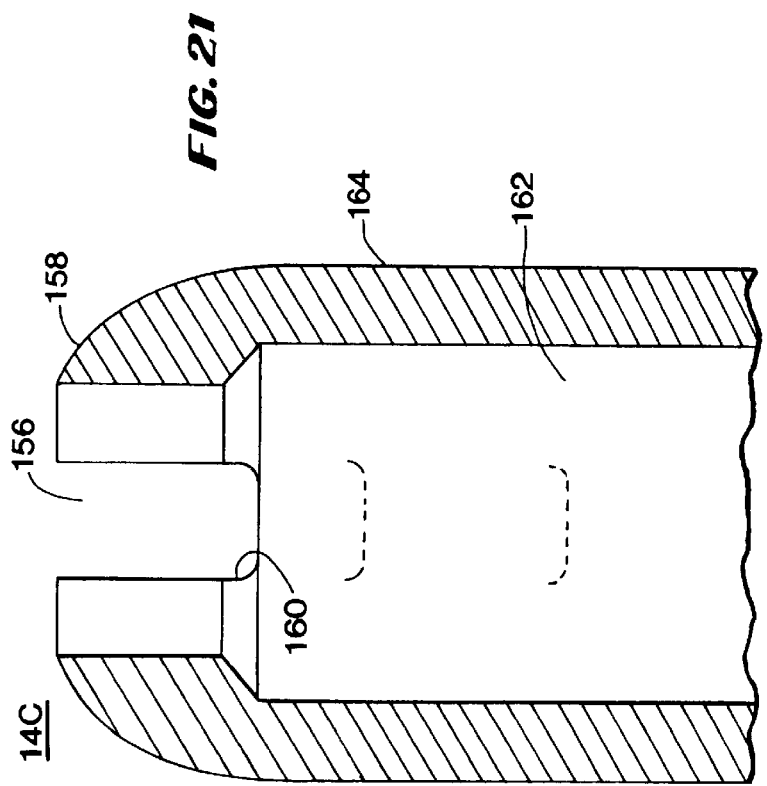
FIG. 21 is a sectional view of a tip usable in the embodiment of FIG. 20.

In FIG. 21, there is shown a fragmentary, sectional view of another embodiment of fragmenting tip 14C having tubular, cylindrical walls 164 enclosing an aspirating section 162, which communicates with the interior of the aspirating tube 18C (FIG. 20). The end of the tip 14C is rounded at 158 and in one embodiment, may be roughened. An opening 156, communicates with the aspirating section 162 and provides a slight, inward pull of tissue.

To fragment tissue, the opening 156 forms a leading edge and a cutting edge in the walls extending below the rotating portion. This opening may be extended to different depths as desired for determining the area of cavitation. Moreover, there may be a slot in one side of the tubular walls 164 communicating with the aspirating section 162 of the fragmenting tip 14C but also, the cavitating edges may be only cut partway into the walls 164 rather than entirely through the walls along their entire length or through only a portion of their length. The slot provides an opening for receiving tissue particles although an opening in conjunction with an edge formed on the surface without penetrating into the aspirating section 162 of the tube may serve the same function.

In operation, the tube 18C is rotated while ultrasonic vibrations are applied along its rotational axis so that it reciprocates in and out of tissue a large number of times for each rotation. For example, the rotation may be between 100 and 15,000 revolutions per minute and preferably between 4,000 and 5,000 revolutions per minute while the ultrasound vibrations may be applied within a range of 10 kilohertz to 500 kilohertz and preferably 40 kilohertz. The exact frequency of reciprocating vibration and rotational speed may be selected by the surgeon and may even extend to lower speeds and frequencies or higher speeds and frequencies depending on the nature of the cataract being fragmented. The tip of the tube should be symmetrical rather than chisel shaped so as to be visible when rotating and reciprocating and may have a continuous distal edge but must be shaped to remove tissue by cavitation.

The frequency of vibration and the speed of rotation are selected so that the tip moves inwardly into the tissue at every small fraction of rotation, such as at every degree of rotation to not impart excessive motion to the mass of the tissue but to cause removal of the tissue as a fine powder.

The combined integrated technology of this surgical tool provides added convenience and functions normally in separate available surgical handpieces. Size reduction due to advancing technology, in conjunction with the physician's desire for smaller surgical wound sites and precision tissue removal, allow this handpiece to incorporate both rotary action and ultrasonic fragmentation. It permits vitrectomy and removal of fragmented cateract with the same handpiece tip. When operating at 40 kHz (which is the most commonly effective frequency for ultrasonic systems), this handpiece delivers 0.012 inch of stroke displacement. The constant stroke feature provides consistent power through any hardness of tissue.

The rotary action assists the ultrasonic fragmentation of the tissue, by tumbling the fractured particles at the distal end of the ultrasonic tip. This allows the tip to acquire a new surface of tissue without the need for a second manipulation instrument. This allows smaller "bites" and reduces propensity for "coring" or "plunging" and subsequent particles are aspirated through the ultrasonic tip.

The added fluid action from the rotation enhances a "capture zone" forming a larger funnel shaped suction pattern that enhances flow to the tip. Just outside this region is a turbulent zone that rejects (protects) tissue. The speed of rotation increases or decreases this action. Working in conjunction with the aspiration and infusion, the rotation enhances the ultrasonic action.

Figure 22:
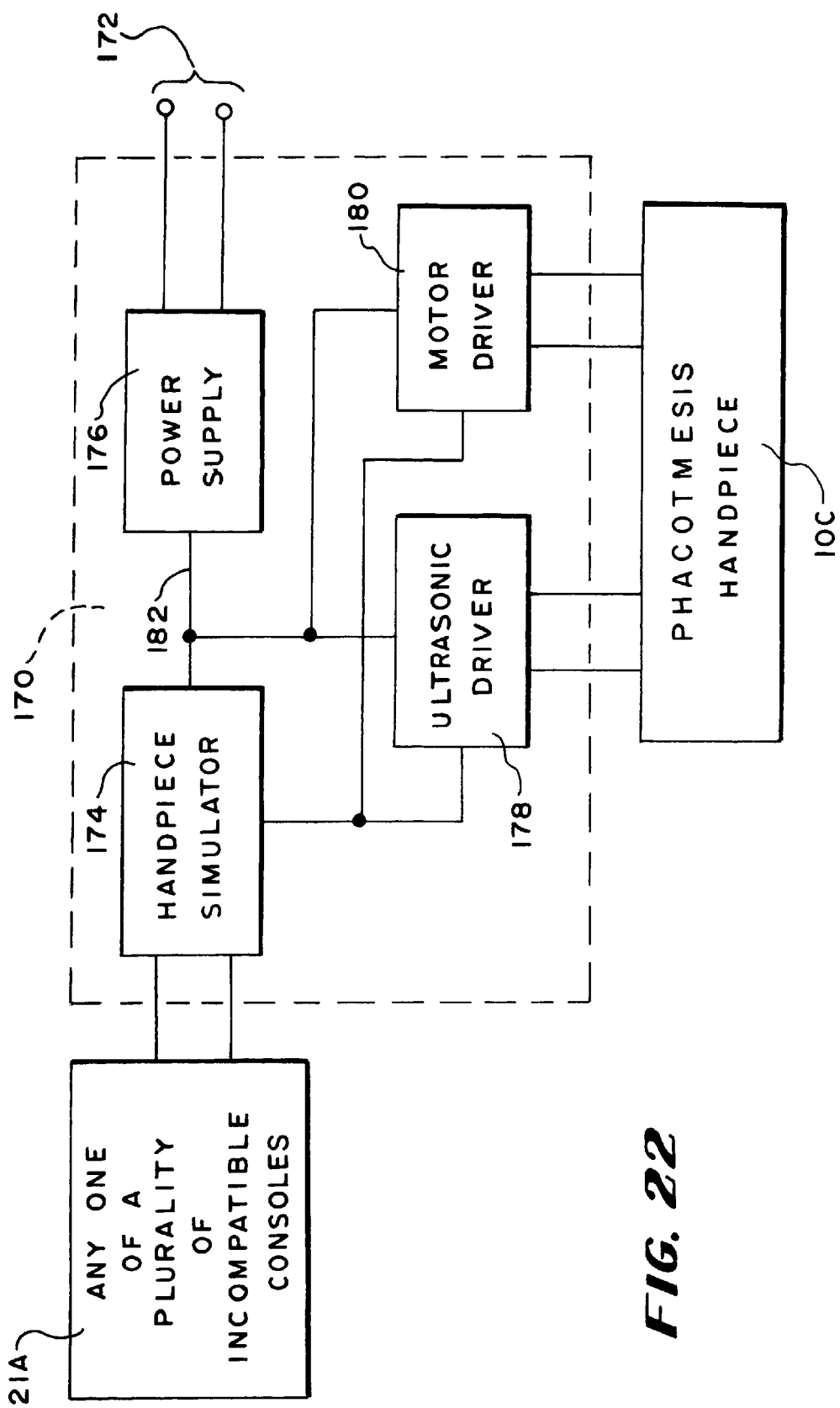
FIG. 22 is a block diagram of a console interface for connecting any of several different consoles to a phacotmesis handpiece and a phacotmesis handpiece.

In FIG. 22, there is shown a block diagram of an interface 170 between a phacotmesis handpiece 10C and any one of a plurality of incompatible consoles 21A which consoles may be electrically incompatible with the phacotmesis handpiece 10C. The consoles 21A may be of the type used for a hydrosonic type of ocular operation or phacoemulsification type of ocular operation.

For this purpose, the interface 170 includes a handpiece simulator 174, a power supply 176, an ultrasonic driver 178, and a motor driver 180. The power supply 176 and the motor driver 180 are conventional. The power supply 176 is adapted to be connected through conductors 172 to conventional power mains. It supplies DC power to the handpiece simulator 174, the ultrasonic driver 178 and the motor driver 180 through the conductor 182.

The handpiece simulator 174 is electrically directly connected to the console 21A and matches the output impedance of the console to the imput impedance of the handpiece to obtain efficient power transfer of the control signal from the console to the drivers. The fluidic connections are connected directly from the console 21A to the phacotmesis handpiece 10C since they are generally compatible. The console 21A and the handpiece simulator 174 together provide the appropriate signal to determine at least the amplitude of ultrasonic vibration by the ultrasonic driver 178. The frequency of the ultrasonic vibrations and the rate of rotation by the motor driver 180 may be set on the handpiece 10C or by the synergist and may or may not be varied by signals from the console 21A depending on the design of the instrument and console.

To enable the connection of a plurality of different consoles to a phacotmesis handpiece 10C, the handpiece simulator 174 includes a rotary switch that is adapted to Interconnect any other of a plurality of different impedances to the input connectors leading to the console 21A, with the input impedances being selected to match the output impedances of the different consoles. Instead of utilizing control signals from the console 21A, the interface 170 may include individual, manually, adjustable attenuation devices or amplifiers to control the ultrasonic driver 178 and the motor driver 180 individually to set rates of ultrasonic vibration of the tip and corresponding rates of rotation of the tip or a combination of the two from a single switch.

Figure 23:
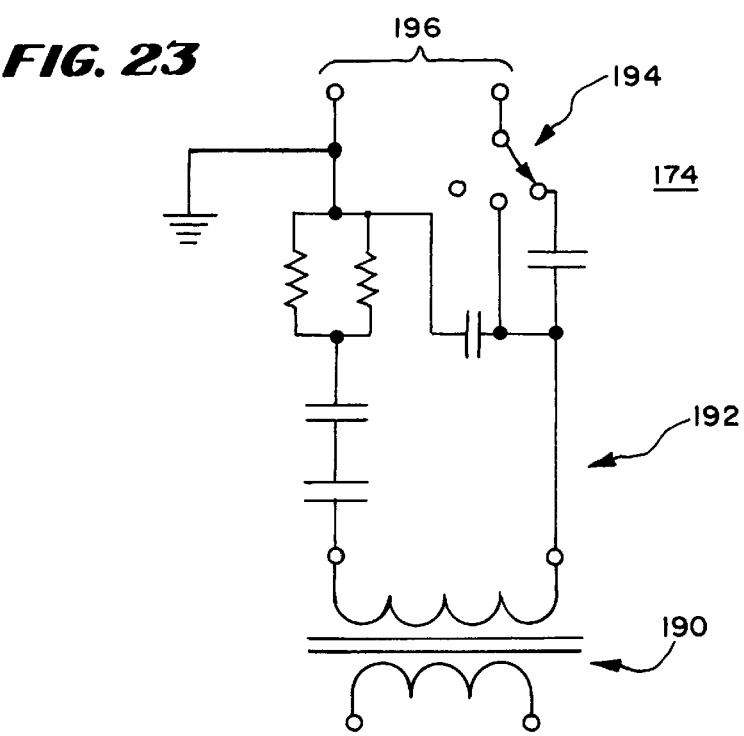
FIG. 23 is a schematic circuit diagram of an interface circuit.

In FIG. 23, there is shown a schematic circuit diagram of the handpiece simulator 174 having an input transformer 190, lumped parameter impedances 192, a selector switch 194, and output terminals 196. The transformer 190 is adapted to have its primary electrically connected to a console 21A (FIG. 22) and the output terminals 196 are adapted to be electrically connected to the ultrasonic driver 178 (FIG. 22) and to the motor driver 180 (FIG. 22). The lumped parameter impedances 192 and the selector switch 194 are adapted to be electrically connected in circuit with each other and between the transformer 190 and the output terminals 196. The switch 194 may be open to disconnect the console, closed to a first terminal to connect one value of impedance or to a second terminal to electrically connect in circuit a second impedance so that the handpiece simulator 174 may provide an input impedance which matches the output impedance of a console to which the handpiece is intended to be connected.

Figure 24:
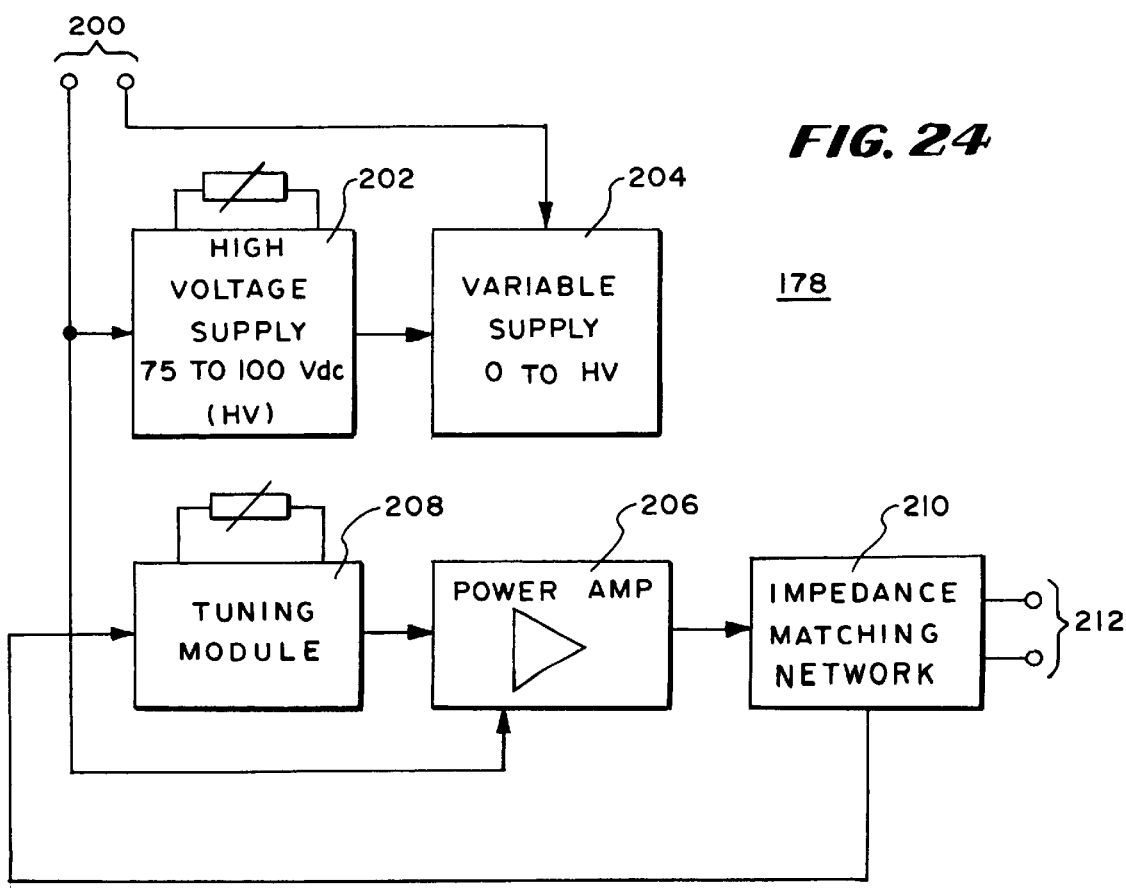
FIG. 24 is a block diagram of an ultrasonic driver circuit.

In FIG. 24, there is shown a block diagram of an ultrasonic driver 178 having input terminals 200, a high voltage power supply 202, a variable power supply 204, a tuning module 208, a power amplifier 206, an impedance matching network 210 and output terminals 212. The input terminals 200 are electrically connected to the handpiece simulator 174 (FIG. 22) to receive control signals. These control signals are applied to drive the DC motor driver 180 (FIG. 22) and are applied to the power amplifier 206 and the variable supply 204. The variable power supply 204 receives power from the high voltage supply 202 and supplies a selected voltage to the power amplifier 206 under the control of the control signal through input terminals 200. This signal determines the amplitude of the signal applied to the impedance matching network 210. The frequency of that signal is adjusted by the tuning module 208 under the control of a computer or the direct control of a surgeon. The output from the matching network 210 drives the ultrasonic vibrator and the handpiece 10C (FIG. 22).

In use, the interface is connected to a console and to the phacotmesis handpiece and the rotary switch is switched to the appropriately labeled console to provide efficient power transfer by impedance matching. In the preferred embodiment, the control signal from the console is used to control both the rotational speed and the vibration speed.

After preparation for phacotmesis, the lens is preferably grooved to form three delineated sections. This may be done by a first groove made in the lens of the eye which is then bifurcated by two grooves, using the phacotmesis instrument described above with the ultrasonically vibrating and rotating tip extending slightly, such as zero to two millimeters beyond the distal end of the irrigating sleeve. After the first groove is made, the nucleus is fractured such as by cracking forceps, then the second groove is made in the larger fragment and that fragment is fractured.

The phacotmesis tip is then retracted slightly until it is level with the irrigation sleeve. It may extend slightly for very hard lens material and may be retracted slightly for soft lens material but is approximately level. The tip is then positioned on a surface of one of the fragments and held by oclusion. The phacotmesis tip is activated and the resulting fragments are one-by-one aspirated.

As can be understood from the above description, the technique and equipment of this invention has several advantages, such as: (1) they selectively fragment some tissue without damaging other nearby tissue; and (2) they are able to fragment, mix and aspirate tissue, and in the case of cataract removal, also scrub the capsular wall without damaging it, all with one instrument.

Although a preferred embodiment of the invention has been described with some particularity, many modifications and variations are possible in the preferred embodiment without deviating from the invention. Therefore, it is to be understood that within the scope of the appended claims, the invention may be practiced other than as specifically described.

What is claimed is:

1. An apparatus for removing tissue from a patient comprising:

means for fragmenting and aspirating tissue having an operative tip;

said means for fragmenting and aspirating tissue comprising means for repeatedly and cyclically moving the operative tip under the control of an electrical signal at a low power level in a first direction and in at least a second direction, wherein the number of cycles per unit time in the first direction is different than in the second direction;

said operative tip having at least one fragmenting surface;

the means for repeatedly and cyclically moving the operative tip including means for rotating the fragmenting surface and means for reciprocating the fragmenting surface at an ultrasonic frequency;

an interface circuit; and said interface circuit including means adapted to be connecting to any one of a plurality of sources of control signals, means for substantially matching the input impedance of said interface circuit to the output impedance of said any one of a plurality of control signals and means for generating at least one control signal from the any one of a source of control signals to control at least one of an ultrasonic driven and a rotational driver;

the size of excursions of the tip in said second direction being controlled by at least one of said at least one control signals.

2. Apparatus in accordance with claim 1 in which the at least one fragmenting surface includes at least one cavitation-creating surface.

3. Apparatus according to claim 1 in which the operative tip includes at least two fragmenting edges and the space between fragmenting edges is less than 5 millimeters.

4. Apparatus according to claim 1 in which the operative tip is tubular and has a diameter of less than 7 millimeters.

5. Apparatus according to claim 1 in which the operative tip is hollow and includes slots extending generally in a plane parallel to the longitudinal axis of the operative tip, said slots having a leading edge and a trailing edge.

6. Apparatus according to claim 1 in which the operative tip is replaceable.

* * * * *